United States Patent [19]

Harris

[11] 4,391,929

[45] Jul. 5, 1983

[54] USEFUL SOLUTIONS OF THE TETRAMETHYLOL DERIVATIVE OF 4,4'ISO-PROPYLIDENEDIPHENOL

[75] Inventor: Thomas G. Harris, Lancaster, Pa.

[73] Assignee: Armstrong World Industries, Inc., Lancaster, Pa.

[21] Appl. No.: 408,670

[22] Filed: Aug. 16, 1982

Related U.S. Application Data

[60] Division of Ser. No. 339,123, Jan. 13, 1980, Pat. No. 4,357,457, which is a continuation-in-part of Ser. No. 178,722, Aug. 18, 1980, abandoned.

[51] Int. Cl.³ ............................................. C08J 9/32
[52] U.S. Cl. .................................... 523/218; 521/133; 521/180; 521/54; 523/219; 525/502; 528/159
[58] Field of Search ................ 523/218, 219; 521/133, 521/180; 528/159; 525/502

[56] References Cited

U.S. PATENT DOCUMENTS

| | | | |
|---|---|---|---|
| 2,912,395 | 10/1959 | Graham | 260/19 N |
| 4,033,910 | 7/1977 | Papa | 260/29.3 |
| 4,112,188 | 9/1978 | Dahms | 260/29.3 |
| 4,131,582 | 12/1978 | Kako et al. | 260/29.3 |
| 4,260,730 | 4/1981 | Sekomakos et al. | 260/29.3 |
| 4,357,457 | 11/1982 | Harris | 523/218 |

*Primary Examiner*—Morton Foelak

[57] ABSTRACT

The tetramethylol derivative of 4,4'iso-propylidenediphenol is dissolved in a solution of water and ethylene or propylene carbonate to yield concentrated solutions of the derivative in a form which may readily be used in the manufacture of foams or used as a liquid binder for molded ceiling products. Based on 100 parts by weight of the tertramethylol derivative, these solutions contain from about 15 to about 35 parts by weight of water and from about 5 to about 30 parts by weight of ethylene carbonate or propylene carbonate, with the total parts by weight of the water and carbonate varying from about 40 to about 45.

2 Claims, No Drawings

USEFUL SOLUTIONS OF THE TETRAMETHYLOL DERIVATIVE OF 4,4′ISO-PROPYLIDENEDIPHENOL

CROSS-REFERENCE TO RELATED APPLICATION

This is a division of application Ser. No. 339,123, filed Jan. 13, 1982, now U.S. Pat. No. 4,357,457 which is a continuation-in-part of U.S. Application Ser. No. 178,722 filed Aug. 18, 1980 in the name of Thomas G. Harris and entitled "Useful Solutions of the Tetramethylol Derivative of 4,4′Iso-Propylidenediphenol," now abandoned.

BACKGROUND OF THE INVENTION

1. Field of the Invention

The invention is directed to useful stable solutions of the tetramethylol derivative of 4,4′iso-propylidenediphenol.

2. Description of the Prior Art

A procedure for forming the tetramethylol derivative of 4,4′iso-propylidenediphenol is disclosed in U.S. Pat. No. 2,912,395. When separated from the water as described in Example 1 of this reference, a wet, oily liquid is recovered. This material, although soluble in water at an elevated temperature, separates out at about 70° C. which limits its utility.

SUMMARY OF THE INVENTION

I have discovered that when ethylene carbonate or propylene carbonate is combined with water and the tetramethylol derivative of 4,4′iso-propylidenediphenol, useful solutions may be formed in which the tetramethylol derivative remains in solution at lower and more conventional processing temperatures. Preferably, based on 100 parts by weight of the tetramethylol derivative, the solutions contain from about 15 to about 35 parts by weight of water and about 5 to about 30 parts by weight of ethylene carbonate or propylene carbonate, or mixtures thereof, with the total parts by weight of the water and the carbonate ranging from about 40 to about 45. These solutions find utility in the manufacture of foams, and the solutions may be also used as binders in forming molded acoustical products.

DETAILED DESCRIPTION

The tetramethylol derivative of 4,4′iso-propylidenediphenol employed herein is prepared by the following procedure (except where otherwise noted):

228.29 parts by weight of 4,4′iso-propylidenediphenol are dissolved in 991.92 parts by weight of an 8.07% aqueous sodium hydroxide solution. 171.22 parts by weight of paraformaldehyde are next added and the mixture maintained at 38° C. for nine hours. The free formaldehyde content is determined at this point and the mixture is then neutralized to a pH of 7.0 by the gradual addition of a 20% aqueous sulfuric acid solution. 3.04 parts by weight of polyoxyethylated nonyl phenol are next added followed by the calculated amount of sodium bisulfite to react with the free formaldehyde. The temperature rises to 60° C. during this stage and crystallization begins. The solid is collected, thoroughly washed, and dried. The product (75% yield) is a light tan solid analyzing 3.75–4.00 mols of formaldehyde reacted per mol of 4,4′iso-propylidenediphenol. It is soluble in water at an elevated temperature (Table I) but separates upon cooling to 70° C. which limits its utility.

When 10% of the water is replaced by ethylene carbonate, the temperature at separation is lowered to 45° C. A 20% replacement lowers the separation temperature of 25° C. Complete replacement of the water by ethylene carbonate no longer yields a useful solution. As shown in Table I, useful resin solutions are formed when about 20 to about 60% of the water in the formulation specified above is replaced by ethylene carbonate.

Based on 100 parts by weight of the tetramethylol derivative, the typical solution will contain from about 15 to about 35 parts by weight water and from about 5 to about 30 parts by weight ethylene carbonate, with the total parts by weight of the water and the carbonate ranging from about 40 to about 45. When all of the water is replaced by ethylene carbonate, the temperature at separation is greater than 80° C.

TABLE I

| Ingredient | Parts by Weight | | | | | | |
|---|---|---|---|---|---|---|---|
| Tetramethylol 4,4′Iso-propylidenediphenol | 100 | 100 | 100 | 100 | 100 | 100 | 100 |
| Water | 42.9 | 38.6 | 34.3 | 23.0 | 17.1 | 14.3 | — |
| Ethylene Carbonate | — | 4.3 | 8.6 | 19.9 | 25.7 | 28.6 | 42.9 |
| Cloud Point (°C.) | 70 | 45 | 25 | — | — | — | >80° C. |
| Viscosity (cps at 40° C.) | | | 200 | 400 | 600 | 810 | |

Surprisingly, propylene carbonate can be used in place of the ethylene carbonate even though it is reported as immiscible in water when present in the range of 17.5 to 93% by weight (Physical Chemistry of Organic Solvent Systems, Covington and Dickinson, 1973, page 11). This is shown in Table II. Since propylene carbonate is reported as being moderately irritating to the mucous membranes of the eyes and respiratory tract, the use of ethylene carbonate is preferred.

TABLE II

| Ingredient | Parts by Weight | |
|---|---|---|
| Tetramethylol 4,4′Iso-propylidenediphenol | 100 | 100 |
| Water | 23 | 23 |
| Ethylene Carbonate | 24.6 | — |
| Propylene Carbonate | — | 24.6 |
| Viscosity (cps at 40° C.) | 510 | 315 |

Phenolic resins based upon 4,4′iso-propylidenediphenol are more resistant to oxidation, i.e., possess better heat stability, than those based upon phenol. Degradation occurs primarily through the methylene linkages and this is interrupted when these linkages are partially replaced by the isopropylidene type linkages. Such improvement has been heretofore limited to nonaqueous systems. The present invention not only permits processing by procedures normally limited to aqueous systems, but also allows modification by water insoluble materials such as epoxy novolacs or unsaturated polyesters.

Examples 1 and 2 illustrate foam formation with this new system, and Examples 3 and 4 illustrate modified systems.

EXAMPLE 1

100.00 parts by weight of tetramethylol 4,4′isopropylidenediphenol were dissolved in 23.00 parts by weight water and 24.60 parts by weight ethylene carbonate by heating to 80° C. with intermittent stirring. The solution formed was cooled to 41° C. and 4.92 parts by weight of a non-hydrolyzable silicone surfactant (Union Carbide L5340), and 9.84 parts by weight of a blowing agent (E. I. duPont Freon 113, $CCl_2F \cdot CClF_2$, B.P. 47.6° C.) were stirred in. High speed agitation was next used to quickly introduce 23.62 parts by weight boric anhydride followed by 24.60 parts by weight of an acid solution consisting of 9.84 parts by weight toluene sulfonic acid, 4.92 parts by weight sulfuric acid, and 9.84 parts by weight water. The blend was immediately placed in a 65° C. oven for fifteen minutes. A white, fine-pored, open-celled foam formed. This foam, after removal and conditioning measured 6.0 lbs./cu. ft. in density.

EXAMPLE 2

100.00 parts by weight of tetramethylol 4,4′isopropylidenediphenol were dissolved in 23.00 parts by weight water and 24.60 parts by weight ethylene carbonate by heating to 80° C. with intermittent stirring. The solution formed was cooled to 75° C. At this point 1.23 parts by weight of a nonionic fluorosurfactant (duPont Zonyl FSN) and 12.30 parts by weight of trichloroethylene (B.P. 113.8° C.) were stirred in. High speed agitation was then used to quickly introduce 7.38 parts by weight boric anhydride followed by 12.30 parts by weight of stannous chloride dihydrate. The blend was placed immediately in a 150° C. oven for five minutes. A white, fine-pored, open-celled foam of 5.9 lbs./cu. ft. density was obtained. This foam, exposed to 350° C., gradually yellows in contrast to that of Example 1 which blackens.

EXAMPLE 3

100.00 parts by weight tetramethylol 4,4′isopropylidenediphenol and 12.3 parts by weight epoxy novolac (epoxy equivalent 175–182, which is employed to provide a more uniform foam) were dissolved in 23.0 parts by weight water and 20.5 parts ethylene carbonate by heating to 80° C. with intermittent stirring. The solution formed was cooled to 40° C. and 3.28 parts by weight of a non-hydrolyzable silicone surfactant (Union Carbide L5340) and 14.35 parts by weight of a blowing agent (duPont Freon 113,$CCl_2F \cdot CClF_2$, B.P. 47.6° C.) were stirred in. High speed agitation was next used to quickly incorporate 14.76 parts by weight boric anhydride followed by 36.90 parts by weight of acid solution of the composition shown in Example 1. The blend was immediately poured into a suitable container and the whole placed in a 65° C. oven for one-half hour. The foam upon removal possessed a density of 3.8 lbs./cu. ft. A 6 in.×6 in. cube showed no exotherm in seven hours at 350° F. A phenolic control foam exothermed in less than two hours.

EXAMPLE 4

An unsaturated elastomeric polyester was prepared from the following starting materials.

| An unsaturated elastomeric polyester was prepared from the following starting materials. | |
|---|---|
| Ingredient | Mols |
| Phthalic Anhydride | 10 |
| Tetrahydrophthalic Anhydride | 40 |
| Trimethylol Propane Mono Allyl Ether | 2 |
| Polyoxyethylene Glycol (M.W. 400) | 35 |
| Ethylene Glycol | 27.5 | by the method described in U.S. Pat. No. 3,703,498. The resultant polyester possessed a hydroxy number of 24.4 and an acid number of 0.5.

100.0 parts by weight of tetramethylol 4,4′isopropylidenediphenol and 12.3 parts by weight of the above polyester were dissolved in 23.0 parts by weight water and 24.6 parts by weight ethylene carbonate by heating to 80° C. with intermittent stirring. The solution formed was cooled to 70° C. and 1.2 parts by weight of a nonionic fluorosurfactant (duPont Zonyl FSN) and 12.3 parts by weight of a blowing agent (duPont Freon 112A, $CCl_2F\text{-}CCl_2F$, B.P. 92.8° C.) were stirred in. High speed agitation was then used to quickly introduce 14.8 parts by weight of boric anhydride followed by 12.3 parts by weight stannous chloride dihydrate. The blend was immediately placed in a 150° C. oven for fifteen minutes. A tough foam of 3.8 lbs./cu. ft. density emerged.

The following examples illustrate tile manufacture.

EXAMPLE 5

100.00 parts by weight of tetramethylol 4,4′isopropylidenediphenol were dissolved in 25.17 parts by weight water and 22.10 parts by weight ethylene carbonate by heating to 80° C. with intermittent stirring. The solution formed was cooled to 40° C. and blended with 147.27 parts by weight expanded perlite (0.12 gm./c.c.) for ten minutes in a Baker Perkin mixer at room temperature. The above was transferred to a 6-inch×6-inch frame and compressed to a thickness of one-half inch. The compacted material was subjected to microwave heating for four minutes in a 700 watt unit. 51.42 parts by weight were lost. The ceiling tile thus formed displayed an indentation (MEP #170) of 39 mils, a modulus of rupture of 34.2 lbs./sq. in., and a density of 28.8 lbs./cu. ft. It displayed only 1.6% by weight moisture pickup after twelve days exposure to 75.5% relative humidity at room temperature, and, 2.0% by weight moisture pickup after twelve days exposure to 96.5% relative humidity at room temperature.

EXAMPLE 6

A phenolic foam (0.033 gm/c.c.) was crushed and passed through a #5 screen (4.00 mm opening). 16.25 parts by weight of this foam and 16.25 parts by weight expanded perlite (0.12 gm/cc) were tumbled together for one minute at room temperature in a Baker Perkins mixer. 32.5 parts by weight of a solution consisting of:

| | |
|---|---|
| tetramethylol 4,4′iso-propylidenediphenol[1] | 100.0 parts by weight |
| water | 31.6 |
| ethylene carbonate | 24.8 |

[1] Prepared in accordance with Example 1 of U.S. Pat. No. 2,912,395.

were then added and mixing continued for an additional five minutes. The mix was transferred to a 6-inch×6- inch frame and compressed to one-half inch. The compressed material was subjected to microwave heating for four minutes in a 700 watt unit. A weight loss of 11.8 parts by weight was observed. The emerging tile displayed a density of 10.0 lbs./cu. ft.

EXAMPLE 7

35.0 parts by weight of perlite (0.12 gm/cc) was mixed with 35.0 parts by weight of a solution consisting of:

| | |
|---|---|
| tetramethylol 4,4'iso-propylidenediphenol[1] | 100.0 parts by weight, |
| water | 31.7 |
| ethylene carbonate | 24.6 |

[1]Prepared in accordance with Example 1 of U.S. Pat. No. 2,912,395 at room temperature in a Baker Perkins mixer. 35.0 parts by weight of the above was uniformly spread at the bottom of a 6-inch×6-inch frame. A piece of a 6-inch×6-inch×¾-inch phenolic foam (0.033 gm/cc) was inserted and the remaining 35.0 parts by weight of mix uniformly spread over its surface. The composite was compressed to one-half inch and subjected to microwave heating for four minutes in a unit capable of delivering 700 watts. The emerging material possessed a density of 12.6 lbs./cu. ft.

What is claimed is:

1. A foam produced by heating an acidified mixture of a solution comprising, in relative proportions, 10 parts by weight of the tetramethylol derivative of 4,4'iso-propylidenediphenol, about 15 to about 35 parts by weight water and about 5 to about 30 parts by weight of ethylene carbonate or propylene carbonate, with the total parts by weight of water and carbonate ranging from about 40 to about 45 with a surfactant and a blowing agent.

2. A ceiling tile produced by mixing expanded perlite with a solution comprising, in relative proportions, 10 parts by weight of the tetramethylol derivative of 4,4'iso-propylidenediphenol, about 15 to about 35 parts by weight water and about 5 to about 30 parts by weight of ethylene carbonate or propylene carbonate, with the total parts by weight of water and carbonate ranging from about 40 to about 45, and compressing and curing the mix.

* * * * *